United States Patent [19]
Phillipps et al.

[11] 3,959,260
[45] May 25, 1976

[54] ANAESTHETIC STEROIDS OF THE PREGNANE AND 19-NORPREGNANE SERIES HAVING A SULFUR-CONTAINING GROUP AT THE 21-POSITION

[75] Inventors: Gordon Hanley Phillipps, Wembley; Robin Lawrence, Stoke Poges; Christopher Earle Newall, London; Michael Wright, Stoke Poges, all of England

[73] Assignee: Glaxo Laboratories Limited, Greenford, England

[22] Filed: July 16, 1974

[21] Appl. No.: 488,989

Related U.S. Application Data

[63] Continuation of Ser. No. 356,097, May 1, 1973.

[30] Foreign Application Priority Data
May 5, 1972 United Kingdom............... 21145/72

[52] U.S. Cl..................... 260/239.5; 260/239.55 R; 260/397.45
[51] Int. Cl.$^2$......................................... C07J 43/00
[58] Field of Search................................ 260/239.5

[56] References Cited
UNITED STATES PATENTS
3,882,151   5/1975   Phillipps et al. ........... 260/239.55 R Primary Examiner—Elbert L. Roberts
Attorney, Agent, or Firm—Bacon & Thomas

[57] ABSTRACT

Steroid anaesthetics of the pregnane and 19-norpregnane series are described, the compounds possessing a 3α-hydroxy group, a 17α-hydrogen atom, a 20-oxo group and at the 21-position the residue of a sulphur nucleophile or a sulphone or sulphoxide grouping.

22 Claims, No Drawings

ANAESTHETIC STEROIDS OF THE PREGNANE AND 19-NORPREGNANE SERIES HAVING A SULFUR-CONTAINING GROUP AT THE 21-POSITION

This is a continuation, of application Ser. No. 356,097, filed May 1, 1973.

This invention is concerned with compounds of the pregnane series having anaesthetic activity.

It has long been known that a number of steroids give rise to profound depression of the central nervous system and act pharmacodynamically as anaesthetics or hypnotics. Such compounds have been the subject of considerable study in an attempt to find anaesthetics to replace such substances as thiopentone sodium normally used but well known to be accompanied by some degree of hazard or disadvantage. The literature shows that very many steroid compounds have been studied in this regard. Reviews and discussions of some of the work carried out are to be found, for example, in "Methods in Hormone Research" (Edited by Ralph I. Dorfman, Vol. III Part A, Academic Press, London and New York, 1964, pages 415–475); H. Witzel, Z. Vitamin Hormon-Fermentforsch 1959, 10, 46–74; H. Selye, Endocrinology, 1942, 30, 437–453; S.K. Figdor et al., J. Pharmacol. Exptl. Therap., 1957, 119, 299–309 and Atkinson et al., J. Med. Chem. 1965, 8, 426–432.

A thorough review of the literature indicates that many anaesthetic steroids possess poor activity and/or long induction periods. A variety of undesired side effects such as paraesthesia and vein damage have also been noted.

We have now found useful anaesthetic activity in a new group of pregnane steroids.

Thus the invention provides steroids of the pregnane or 19-norpregnane series possessing a 3α-hydroxy group, a 17α-hydrogen atom, a 20-oxo group, and at the 21-position the residue of a sulphur nucleophile or a sulphone or sulphoxide grouping, there being a 5α-hydrogen atom when a 21-acetylthio group is present in a saturated or otherwise unsubstituted 3α-hydroxy-pregnane-11,20-dione and, where the steroids carry basic groups, the acid addition salts thereof.

The invention also provides pharmaceutical compositions containing an anaesthetic compound in accordance with the invention and processes for the preparation of the compounds of the invention.

21-Acetylthio-3α-hydroxy-5β-pregnane-11,20-dione is however a known compound but it is known to give highly undesirable side effects when administered as a suspension in physiological saline containing 0.4% Tween 80. It is to be understood that the invention does not include this compound or its preparation or compositions containing it in the form of a suspension. It is surprising that other 21-thio derivatives should exhibit such marked and useful anaesthetic activity.

The compounds of the invention may possess substituents at other positions of the steroid nucleus, for example at the 2, 3β, 11 or 16 positions. They may also be unsaturated, for example at the $\Delta^{8(9)}$ and/or $\Delta^1$ or $\Delta^4$ positions. When a hydrogen atom is present at the 5-position it may be in either the α or β configuration, preferably the α configuration. Compounds in the pregnane series are generally preferred.

Compounds having an oxo group at the 11-position are preferred, especially when a 5α-hydrogen atom is present.

In general, the compounds of the invention are good anaesthetics with generally short induction periods, the anaesthetic action at suitable doses being in general instantaneous; these compounds are thus excellent anesthetics for inducing anaesthesia which is to be maintained e.g. by an inhalation anaesthetic such as ether, halothane, nitrous oxide, or trichloroethylene. The compounds are however capable of maintaining anaesthesia and analgesia to a sufficient degree to enable various surgical operations to be conducted without the aid of an inhalation anaesthetic, the required degree of anaesthesia being maintained if necessary by repeated administration (or even continuous administration). Moreover, the said anaesthetics in accordance with the invention in general give rise to minimal side-effects as compared to many previously described steroidal anaesthetics.

It will be appreciated that the sulphone and sulphoxide substituents may be regarded as oxidised derivatives of the thioether nucleophile residues.

The 21-substituent may generally be defined as a group of the formula

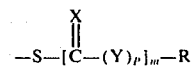

in which X and Y, which may be the same or different, are sulphur or oxygen and m and p, which may be the same or different, are each 0 or 1; and R is an aliphatic, cycloaliphatic, araliphatic, aryl or carbon attached heterocyclic group, or when $m = 1$ and $p = 0$ and N-attached residue of a primary or secondary amine (including secondary heterocyclic amines) or ammonia, or when $m = 0$ a cyano group or a hydrogen atom. The invention also includes the sulphinyl and sulphonyl derivatives of the groups of the formula I, in which $m = 0$. Preferably X is sulphur when $p = 1$.

Examples of aliphatic groups are alkyl, alkenyl and alkynyl groups which may be unsubstituted or substituted by, for example, an N-attached residue as defined above or halogen (e.g. chlorine) atoms.

Aryl groups may for example be monocyclic aryl groups such as phenyl groups, which may for example be substituted by alkyl, alkoxycarbonyl, alkylthio, nitro groups or halogen (e.g. iodine) atoms.

Araliphatic groups may for example be aralkyl, aralkenyl or aralkynyl groups in which the aryl portions may be just described. Cycloaliphatic groups may for example be cycloalkyl groups or substituted cycloalkyl groups, e.g. cyclohexyl groups.

Carbon-attached heterocyclic groups may be saturated or unsaturated, may be mono-cyclic (such as pyridyl) and may contain further hetero atoms such as nitrogen, oxygen or sulphur.

Primary or secondary amines may for example be monoalkyl or dialkylamines, which may be substituted, for example by hydroxy, oxo, alkoxy, acyloxy or alkoxycarbonyl groups; or more preferably heterocyclic amines, which are preferably monocyclic and may contain a further hetero atom such as nitrogen, oxygen or sulphur. The heterocyclic amines may be substituted (e.g. by one or more alkyl, aralkyl, aryl, e.g. phenyl, hydroxy, oxo, alkoxy, alkoxycarbonyl or acyloxy groups) or unsubstituted (e.g. morpholino, piperidino or thiamorpholino), saturated or unsaturated.

In all the cases referred to above, the alkyl, alkenyl and alkynyl groups and the corresponding portions of araliphatic groups preferably have 1 to 6 carbon atoms. Heterocyclic groups may generally contain 5 to 10, e.g. 5 or 6, ring members.

The 21-thio-substituent may be a group of the formula -SCN, -SCO.$R^1$, -SCS.$OR^2$, -$SR^3$ (including -SH), -SCS.$R^2$ or -SCS.$SR^3$ while the sulphinyl and sulphonyl groups may have the formulae -SO.$R^3$ or -$SO_2$.$R^3$, where $R^1$, $R^2$ and $R^3$ are R as defined above.

21-Acylthio compounds and 21-xanthates, containing the groups -SCO.$R^1$ and -SCS.$OR^2$ respectively, are generally preferred on account of their superior anaesthetic properties. Certain other of the compounds, particularly those containing a 21-SH or -SO.$R^3$ group, are also useful as intermediates in the preparation of other compounds in accordance with the invention.

In the acylthio compounds of the invention, i.e. those with a 21-SCO.$R^1$ group, $R^1$ may for example be a substituted or unsubstituted alkyl, alkenyl, alkynyl, aryl, aralkyl, aralkenyl, aralkynyl or carbon-attached saturated or unsaturated heterocyclic group.

The alkyl groups may be substituted for example by a substituted or unsubstituted amino group, preferably a nitrogen containing heterocyclic group which has 5 or 6 ring members and may contain a further hetero atom such as oxygen, sulphur or nitrogen, e.g. a morpholino thiamorpholino or thiazolidino group; or by a halogen (e.g. chlorine) atom.

The aryl groups are preferably monocyclic, such as phenyl, and may for example be substituted by alkyl, alkylthio, alkoxycarbonyl, or nitro groups or halogen (e.g. iodine) atoms, preferably in the ortho position.

The heterocyclic groups may be monocyclic, saturated or (more preferably) unsaturated and contain 5 to 10 ring members. The hetero atom is preferably nitrogen and a further hetero atom such as nitrogen, oxygen or sulphur may also be present.

Examples of $R^1$ are methyl, phenyl, o-iodophenyl, o-nitrophenyl, o-ethoxycarbonylphenyl, morpholinomethyl, 1-morpholino-n-butyl, thiamorpholinomethyl, pyrid-2- and -3-yl, piperidinomethyl, o-methylthiophenyl, 1,2,5,6-tetrahydropyridinomethyl, 2'-chloroethyl, n-propyl, n-butyl, 2'-morpholinoethyl and 3'-morpholinopropyl.

$R^2$ may for example be a group of the formula -$NR^7R^8$ where $R^7$ and $R^8$, which may be the same or different are substituted or unsubstituted alkyl (e.g. methyl) groups or together with the nitrogen atom form a heterocyclic ring which may contain a further hetero atom such as oxygen, nitrogen or sulphur, e.g. morpholino and thiamorpholino.

$R^2$ may further be a group -$R^6NR^7R^8$ where $R^6$ is an alkylene group preferably having 1-6 carbon atoms and $R^7$ and $R^8$ together with the nitrogen atom form a heterocyclic ring.

In the xanthates $R^6$ is preferably an alkylene (e.g. $C_{1-6}$) group and preferred groups are aminoalkyl groups in which the amino nitrogen atom is a member of a heterocyclic ring; an example of a xanthate $R^2$ group is morpholinoethyl.

In the dithiocarbamates $R^6$ represents a carbonnitrogen bond. Examples of such -$NR^7R^8$ groups are morpholino and dimethylamino.

$R^3$ may for example be a substituted or unsubstituted alkyl, alkenyl, alkynyl, aralkyl, aralkenyl, aralkynyl or carbon-attached saturated or unsaturated heterocyclic group. The alkyl groups may be substituted for example by amino or substituted amino groups, i.e. preferably amino groups in which the amino nitrogen atom is a member of a saturated or unsaturated heterocyclic ring. The aryl portions of the aralkyl groups are preferably monocyclic, e.g. phenyl.

Examples of such groups are iso-propyl, n-butyl, ethyl, morpholinoethyl, pyrid-2-yl and benzyl.

Examples of substituents which may be present at the 2β-position include an acyloxy group having for example 1 to 9 carbon atoms, an ether or thioether group (i.e. the residue of an alcohol, a phenol or a thiol) containing for example 1–9 carbon atoms (e.g. methoxy), an alkyl or cycloalkyl group for example containing up to 9 carbon atoms, an aryl group (e.g. a phenyl group), an aralkyl group (e.g. a benzyl group), a hydroxy group, a thiocyanato group, a nitro-oxy group, or a halogen atom.

Acyloxy substituents (which may be saturated or unsaturated) include lower ($C_1$-$C_6$) alkanoyloxy groups, (substituted if desired, for example, with one or more halogen, e.g. chlorine atoms, lower alkoxy, amino or substituted amino groups), aroyloxy groups (e.g. a benzoyloxy group), or aralkanoyloxy groups (e.g. a phenylacetoxy group).

Ether substituents, which may be saturated or unsaturated, include lower ($C_1$-$C_6$) alkoxy groups, lower alkenyloxy groups (e.g. an allyloxy group), cycloalkoxy groups (e.g. a cyclohexyloxy group), aryloxy groups (e.g. a phenoxy group) and aralkoxy groups (e.g. a benzyloxy group). Thioether groups corresponding to the above-mentioned ether groups are representative of 2β-thioether substituents.

The 2β-substituent may alternatively be an azido, sulphonyloxy (e.g. tosyloxy) group or an acylthio group.

Examples of 2β-alkyl groups include especially lower alkyl groups containing 1–5 carbon atoms such as methyl, ethyl, propyl, butyl, isobutyl and t-butyl groups. An example of a cycloalkyl group is a cyclohexyl group.

Examples of lower alkanoyloxy 2β-substituents include acetoxy, propionloxy, butyryloxy piperidinoacetoxy, morpholinoacetoxy, diethylaminoacetoxy and chloroacetoxy groups. Examples of lower alkoxy groups include methoxy, ethoxy, propoxy, isopropoxy, n-butoxy and t-butoxy groups, and the corresponding thio compounds exemplify lower alkyl thio substituents.

Lower alkoxy and lower alkylthio substituents at the 2β-position may themselves be substituted for example by one or more halogen (e.g. chlorine) atoms, lower alkoxy, esterified carboxyl (e.g. ethoxycarbonyl), hydroxy, amino or substituted amino (e.g. morpholino) groups, or substituted or unsubstituted acyloxy (e.g. morpholinoacetoxy, chloroacetoxy or diethylaminoacetoxy), or heterocyclic groups, e.g. a tetrahydrofuranyl group. Alkyl, cycloalkyl and aryl groups may also be substituted.

The 2β-position may also carry amino substituents, e.g. amino or substituted amino groups, for example mono- or di-alkylamino or saturated, unsaturated or aromatic heterocyclic amino groups, e.g. a morpholino group.

Particularly important 2β-substituents are ethoxy and methoxy groups.

Examples of substituents which may be present at the 2α-position are alkyl groups, e.g. having 1 to 6 carbon atoms such as methyl or ethyl, or halogen atoms, e.g. chlorine or bromine.

Examples of substituents which may be present at the 3β-position are alkyl groups, e.g. having 1 to 6 carbon atoms such as methyl, ethyl or pentyl.

An oxo group may be present at the 11-position and compounds having this substituent are particularly important. Alternatively, a hydroxy group may be present at the 11-position, in either the α configuration or, in the presence of absence of an α-alkyl or alkenyl ($C_{1-6}$) group (e.g. methyl or allyl) in the β configuration. Another possible grouping is an epoxy group linked also to the 9-position.

The 16-position may be substituted by one or more alkyl or alkoxy groups having 1 to 6 carbon atoms (e.g. methyl, ethyl, methoxy, or gem-dimethyl) or by a halogen atom (e.g. fluorine or chlorine). A single 16-substituent may be in the α or β configuration.

Certain of the compounds of the invention, e.g. those containing a basic nitrogen atom, are capable of forming acid addition salts and this has the advantage of tending to improve the water solubility of the compounds. Such salts include, in the case of aminosubstituted compounds, hydrochlorides, hydrobromides, phosphates, sulphates, p-toluenesulphonates, methanesulphonates, citrates, tartrates, acetates, ascorbates, lactates, maleates and succinates.

When these salts are used as anaesthetics they should be non-toxic, i.e. physiologically acceptable in the dosage at which they are administered. Other salts may, however, be of use in for example, isolation of the product from a synthetic reaction.

Particularly preferred compounds in accordance with the invention by virtue of their excellent anaesthetic properties are:

1. 3α-Hydroxy-21-thiocyanato-5α-pregnane-11,20-dione;
2. 21-Acetylthio-3α-hydroxy-5α-pregnane-11,20-dione;
3. 21-Acetylthio-2β-methoxy-3α-hydroxy-5α-pregnane-11,20-dione;
4. 3α-Hydroxy-21-pyrid-3'-ylcarbonylthio-5α-pregnane-11,20-dione;
5. 3α-Hydroxy-21-benzoylthio-5α-pregnane-11,20-dione;
6. 3αHydroxy-21-morpholinoacetylthio-5α-pregnane-11,20-dione;
7. 3α-Hydroxy-21-morpholinoacetylthio-5α-pregn-1-ene11,20-dione;
8. 2β-Ethoxy-3α-hydroxy-21morpholinoacetylthio-5α-pregnane-11,20-dione;
9. 3α-Hydroxy-21(2'-morpholino-n-valerylthio)-5α-pregnane-11,20-dione.
10. 3α-Hydroxy-3β-methyl- 21-morpholinoacetylthio-5α-pregnane-11,20-dione; and
11. 3αHydroxy-21-thiamorpholinoacetylthio-5α-pregnane-11,20-dione;
12. 21-(3'-Chloro-n-propionylthio)-3α-hydroxy-5α-pregnane-11,20-dione;
13. 21-(n-Butyrylthio)-3α-hydroxy-5α-pregnane-11,20-dione;
14. 3α-Hydroxy-21-morpholinoethoxythiocarbonylthio-5α-pregnane-11,20-dione;

and the salts of those compounds which are basic.

PHARMACEUTICAL FORMULATIONS

The anaesthetic compounds of the invention may be formulated as convenient, following generally known pharmaceutical practices, (including both human and veterinary medical practices), with the aid of one or more pharmaceutical carriers or excipients. For anaesthetic purposes, the steroids will be given by injection and thus one aspect of this invention comprises an anaesthetic composition for parenteral administration comprising an anaesthetic compound in accordance with the invention in a parenterally acceptable vehicle.

When the anaesthetic compounds are sufficiently soluble in water (e.g. the salts, particularly those referred to above) they may be formulated in aqueous solutions (e.g. isotonic sterile solutions) or supplied as powders for dissolution in a sterile medium before use. Many of the anaesthetic steroids of the invention are poorly soluble in water. We have found however that they may be formulated for parenteral administration in an aqueous solution of a parenterally acceptable non ionic surface active agent. These surface active agents may also be used even where the steroid is sufficiently water soluble as they may reduce the risk of thrombophlebitis.

We have further found that, most surprisingly, the compound 21-acetylthio-3α-hydroxy-5β-pregnane-11,20-dione, although having undesirable properties when tested in a suspension, is substantially free from such side effects when formulated in solution in an aqueous non-ionic surfactant; the invention therefore extends to such surfactant solutions containing this steroid.

The non-ionic surface active agents used for the purpose of this invention are generally those of the water-soluble type, conveniently having an HLB value of at least 9, preferably at least about 12, advantageously at least about 13. Preferably the HLB value of the surface active agent is not greater than about 18. A mixture of surface agents may be used, in which case it is the HLB value of the mixture which is conveniently between the values just mentioned.

The surface active agent must naturally be one which is physiologically compatible, i.e. of itself give rise to no physiologically unacceptable side effects in the dosages employed in the intended species to be treated (man or animal).

Surface active agents for use in accordance with the invention are for example to be found among the following non-ionic surfactants and classes of surfactants:-

Polyoxyethylated derivatives of fatty (C12-C20) glyceride oils, e.g. castor oil, containing from 35 to 60 oxyethylene groups per mole of fatty oil. Polyoxyethylene ethers (containing from 10 to 30 oxyethylene groups) of long chain alcohols (containing for example from 12–18 carbon atoms).

Polyoxyethylene-polyoxypropylene ethers containing from 5 to 150 and from 15 to 50 oxyethylene and oxypropylene groups respectively. Polyoxyethylene ethers (containing from 6 to 12 oxyethylene groups) of alkyl phenols the alkyl groups of which preferably contain 6-10 carbon atoms.

Polyoxyethylated (containing from 15 to 30 oxyethylene groups) fatty acid (e.g. C12-18) esters of sugar alcohol anhydrides e.g. sorbitan or mannitan.

Long-chain (e.g. C10-16) alkanoyl mono- and dialkanolamides (the alkanol portions of which for example contain 1-5 carbon atoms) for example lauroyl monoand di-ethanolamides. Polyethylene glycol esters (containing from 6 to 40 ethylene oxide units) of long chain fatty acids (containing for example 12-18 carbon atoms) e.g. polyethyleneglycol monooleate (containing for example 8 ethylene oxide units).

Other useful surfactants include phospholipids such as lecithins, e.g. egg or soyabean lecithins.

Examples of non-ionic surface active agents, of the foregoing types, useful in accordance with the invention include:

Cremophor EL, a polyoxyethylated castor oil containing about 40 ethylene oxide units per triglyceride unit;

Tween 80, polyoxyethylene sorbitan monooleate containing about 20 ethylene oxide units;

Tween 60, polyoxyethylene sorbitan monostearate containing about 20 ethylene oxide units; and Tween 40, polyoxyethylene sorbitan monopalmitate containing about 20 ethylene oxide units.

The expression "solutions" is used herein to denote liquids which have the appearance of true solutions and are thus optically clear and capable of passage, for example, through a micro-porous filter, irrespective of whether such solutions are true solutions in the classical chemical sense and irrespective of whether they are stable or metastable. Thus it may be that the steroid is associated with micelles. The solutions of this invention, irrespective of their precise physical nature, behave as true solutions for the practical purpose of intravenous injection.

The proportion of surface active agent to be used in the compositions of this invention depends upon its nature and upon the concentration of steroid desired in the final composition.

In preferred compositions according to the invention the proportion of surfactant is preferably at least 5% by weight and advantageously above 10% by weight. A very convenient proportion of surfactant has been found to be 20% by weight but 30% and up to 50% may be used. The proportions of surfactant are expressed by weight in relation to the total volume of the composition.

In one method of preparing the solutions comprising a surfactant, the steroid is first dissolved in the selected surfactant, for example with heating, and the resulting solution dissolved in water. Alternatively the steroid may be dissolved in a volatile organic solvent advantageously having a boiling point of less that about 80°C which is miscible with the surface active agent such as a volatile lower aliphatic ketone e.g. acetone or methyl ethyl ketone or a volatile halogenated hydrocarbon e.g. chloroform or methylene chloride. The surface active agent is then added to this solution, the organic solvent removed by evaporation, for example by passing a stream of an inert gas through the solution e.g. nitrogen and the resulting solution of steroid in surfactant is mixed with water.

The solutions may also be prepared by shaking the steroid with an aqueous solution of the surface active agent.

In all cases simple tests enable one to determine the relative proportions of surface active agent required.

As will be clear, the proportion of steroid which is dissolved in the aqueous medium according to the invention depends upon the water-solubility of the steroid and, where present, the nature and amount of surface active agent used. The composition will generally contain at least 1 mg/ml of steroid but solutions can be made containing for example up to 11 mg/ml of steroid or even 50 mg/ml. The more concentrated solutions can usually only be made with the water-soluble steroids.

The anaesthetic solutions according to the invention are generally administered by intravenous injection although as is known in the anaesthetic art in certain cases, e.g. with young children, intramuscular injection might be preferred.

As is usual in the case of anaesthetics, the quantity of steroid used to induce anaesthesia depends upon the weight of the individual to be anaesthetised. For intravenous administration in the average man a dose of from 0.2 to 10 mg/kg will in general be found to be satisfactory to induce anaesthesia, the preferred dose being within the range of from 0.5 to 3.5 mg/kg. The dose will naturally vary to some extent dependent upon the physical condition of the patient, and the degree and period of anaesthesia required, all as is well known in the art. It is thus possible by adjustment of the dose to achieve durations of anaesthesia varying from about 10 minutes to up to an hour or more. If it is desired to maintain prolonged anaesthesia, repeated doses of the solutions of this invention may be used, such repeated doses being generally either of the same order or lower than the original dose. Alternatively continuous administration may be undertaken at for example a rate of 0.025-2.0 (preferably 0.09 – 1.4) mg/kg/min.

Where the anaesthetic solutions are administered intramuscularly, higher doses are generally necessary.

COMPOUND PREPARATION

The compounds of the invention having at the 21-position the residue of a sulphur nucleophile may in general be prepared by reacting a corresponding steroid of the pregnane or 19-norpregnane series possessing a 3α-hydroxy group, a 17α-hydrogen atom, a 20-oxo group and a readily eliminatable substituent at the 21-position, with a sulphur nucleophile whereby the residue of a sulphur nucleophile is introduced at the 21-position.

The starting 21-substituted steroid is preferably the corresponding 21-bromo steroid, but other compounds may be used, for example a corresponding 21-chloro, 21-iodo or 21-sulphonyloxy (e.g. methanesulphonyloxy)compound.

The compounds of the invention are preferably prepared by reacting the starting 21-substituted compound with a source of an ionic form of the 21-thio substituent. In many cases this source can be a salt of a thioacid corresponding to the thio substituent, e.g. an alkali metal or alkaline earth metal salt such as a sodium, potassium, calcium or barium salt, a tertiary or quaternary ammonium salt or, where the substituent contains a basic nitrogen atom, an internal salt.

Thus, the acylthio compounds of the invention containing a 21-SCO.R$^1$ group may be prepared by reacting the starting 21-substituted compound with a salt of the acid HSCO.R$^1$. The reaction may be carried out in any suitable inert solvent, preferably a polar organic solvent in the presence or absence of water e.g. a a nitrile solvent such as acetonitrile, an alkano solvent such as ethanol or methanol, an amide solvent such as dimethylformamide or dimethylacetamide, a cyclic ether uch as dioxan or tetrahydrofuran, a sulphone solvent such as dimethylsulphone or a sulphoxide solvent such as dimethylsulphoxide. The preferred solvent is acetone. The reaction may be carried out at any suitable temperature up to reflux.

Xanthates containing the 21-SCS.OR$^2$ group may similarly be prepared by the use of a salt of the acid HSCS.OR$^2$. Dithioesters and particularly dithiocarbamates containing the 21-SCS.R$^2$ group may similarly be prepared by the use of salts of acids of the formula HSCS.R$^2$. Trithiocarbonates containing the 21-SCS.SR$^3$ group may similarly be prepared by the use of a salt of an acid of the formula HSCS.SR$^3$. The thiocyanates may similarly be prepared by the use of thiocyanate salt.

In general the salts required for the above preparations, if not readily available, may be prepared from known compounds by generally known techniques.

Thus for example alkali metal (e.g. sodium) xanthates may be prepared by first forming an alkoxide of the formula R$^2$OM (where M is an alkali metal) by, for example, reacting the alcohol R$^2$OH with the alkali metal in a solvent such as toluene, and then reacting the alkoxide with carbon disulphide.

Compounds containing a 21-SH group may be prepared by the hydrolysis, preferably under acid conditions, of a corresponding 21-acylthio compound.

Compounds having a 21-acylthio group may also be prepared from the latter 21-thiols by acylation, and this method is convenient in cases where the acid HSCOR$^1$ is not readily obtainable. The acylation may be carried out by conventional methods using a reactive derivative of the acid R$^1$COOH, such as an acid halide, in the presence of an acid binding agent (e.g. an organic terteary base such as pyridine). Alternatively, when using a reactive derivative such as an anhydride (e.g. a mixed anhydride such as a trifluoroacetic anhydride), the reaction is preferably carried out in the presence of an acid (e.g. a mineral or organic acid such as p-tuluenesulphonic acid or a Lewis acid such as boron trifluoride) or a base (e.g. pyridine). If necessary, the 3α-hydroxy group may be protected during this reaction, for example, as a tetrahydropyranyl ether or nitrate ester.

Aminoacylthio compounds may be prepared by reacting an amine (e.g. morpholine) with a haloacylthio (e.g. a chloroalkanoylthio) compound.

Thioethers containing the 21-SR$^3$ group may be prepared from the starting 21-substituted compounds referred to above, particularly the corresponding 21-bromo compound, by reaction with a thiol R$^3$SH in the presence of a strong base, e.g. an alkali metal alkoxide such as sodium isopropoxide or an alkali metal hydride such as sodium hydride. The reaction is preferably carried out in a polar solvent medium (e.g. an alkanol solvent such as isopropanol or a ketone, ether, sulphone or sulphoxide solvent such as referred to above). The latter solvents may be used in admixture with a hydrocarbon solvent such as toluene. A preferred solvent medium when the base is an alkali metal isopropoxide is a mixture of toluene and a small amount of isopropanol. The reaction may be carried out at any temperature up to reflux, preferably at a comparatively high temperature.

The 21-sulphinyl and sulphonyl compounds in accordance with the invention may be prepared from the corresponding 21-thioethers by the stepwise oxidation thereof. This oxidation may be effected with a peracid such as peracetic acid, or, preferably, m-chloroperbenzoic acid, or with aqueous hydrogen peroxide. About one equivalent of the oxidising agent is required for the preparation of a sulphinyl compound, and two or more equivalents for the sulphones. An inert solvent, e.g. a chlorinated hydrocarbon such as methylene chloride, is preferably used in this reaction. The reaction is preferably carried out at a low temperature, e.g. $-5$ to $+25°C$.

The 21-substituted compounds used as starting materials in the preparation of the compounds of the invention may readily be prepared from known compounds by conventional methods. A 21-bromo compound, for example, may be prepared by bromination of the corresponding 21-unsubstituted compound, for example with molecular bromine in a solvent such as methanol or ethanol. The reaction is preferably effected at a temperature of $-10$ to $+30°C$. If desired, the reaction may be accelerated by a catalyst such as hydrogen bromide (in acetic acid) or acetyl chloride.

In the preparation of compounds in accordance with the invention possessing an optional substituent or a carbon-carbon double bond such as described above, it is convenient for this substituent or unsaturation to be present in the 21-substituted starting material. Alternatively, these substituents or unsaturation may be introduced subsequently, for example by generaly known techniques using known compounds as starting materials. For convenience a number of methods of introducing the desired substituents or unsaturation into a 3-oxygenated- 20-oxo-pregnane are set out below; certain of these methods are new.

Substitution at the 2β-position in the 5α series can be effected for example by way of the corresponding 2α,-3α-epoxy compound. The epoxy compound itself may be prepared by first dehydrating a 3-hydroxy compound to give the corresponding $\Delta^2$ compound (e.g. by first tosylating the hydroxy group and then detosylating the product), and then treating the $\Delta^2$ compound with a peracid to form the 2α,3α-epoxide ring.

A 2β-substituent may then be introduced by the method described in copending Phillipps etal U.S. Pat. Application Ser. No. 197915 filed Nov. 11, 1971. This general method may be used to introduce all the 2β-substituents described above.

Methods for introducing substituents at the 2α, 3β, 11 and 16 positions are described in copending U.S. Pat. Applications of Cook etal Ser. No. 208959 filed Dec. 16, 1971 and Gregory etal Ser. No. 194918 filed Nov. 2, 1971. These or analogous methods may be used to introduce all the substituents referred to above at these positions. For example, an 11-alkenyl or 16-alkyl group may be introduced by methods analogous to those described in U.S. Pat. Application No. 208959 for the introduction of an 11-allyl or 16-methyl substituent.

5α-Steroids possessing $\Delta^1$ unsaturation may also be prepared by known methods, but we prefer to use a method which comprises converting a 2β-bromo-3α-hydroxy pregnane into its corresponding 2β,21-dibromo compound, if desired protecting the 3α-hydroxy group (e.g. as its tetrahydropyranyl ether), dehydrobrominating to give the $\Delta^1$ compound, and then deprotecting the product where necessary to give the desired 1,2-dehydro-3α-hydroxy-20-oxo-21-bromo compound.

The dehydrobromination may be effected, for example using a nitrogen containing Lewis base such as a di-lower alkyl lower acylamide e.g. dimethylformamide or dimethylacetamide advantageously in the presence of an alkali metal or alkaline earth metal carbonate, for example calcium carbonate.

In general it has been found convenient to effect the dehydrobromination at an elevated temperature for example from 80° to 170°C. Lower temperatures may be employed when a lithium or calcium halide is present.

Compounds possessing $\Delta^4$ unsaturation may be prepared from $\Delta^3$-steroids by methods analogous to those described for obtaining the $\Delta^1$ compounds from $\Delta^2$ steroids. Alternatively, $\Delta^4$-steroids may be obtained by the methods described in U.S. Pat. Application No. 194918.

Compounds having a double bond between the 8-and 9-positions and an 11-oxo group may be prepared for example by the method described in U.S. Pat. Application No. 208959. These compounds may also be prepared by dehydration of the corresponding 9α-hydroxy compound, for example using thionyl chloride in pyridine.

5α-Steroids of the invention may also be prepared from the corresponding 3-oxo compounds by stereospecific reduction, e.g. by the method of Browne and Kirk (J. Chem. Soc. C, 1969, 1653) or by the method of Clayton etal U.S. Patent Application Ser. No. 305246. The latter method preferably uses a preformed iridium catalyst reduction system. For example, a reduction system may be prepared from an iridium acid or salt (e.g. chloroiridic acid), trivalent phosphorus compound such as a phosphorous acid ester (e.g. trimethyl phosphite), water and an organic reaction medium (e.g. an alcohol such as isopropanol). The reduction system is then neutralised (e.g. to a pH of 6 to 8.5) with an organic base such as a secondary or tertiary amine (e.g. triethylamine) and reacted with the steroid. When the catalyst system is preformed by heating at reflux for 16 to 72 hours, the reduction can be accomplished in 2-3 hours at reflux; longer times may be necessary at room temperature.

5β-Steroids may similarly be prepared by hydride reduction of 3-oxo steroids.

In the preparative methods described above, it may be desirable to protect a 3α-hydroxy or 20-oxo group during the reaction, the protection being subsequently removed to regenerate the hydroxy or oxo group. A 3α-hydroxy group may for example be protected in the form of a nitrate ester or a tetrahydropyranyl ether. A 20-oxo group may be protected as a ketal and regenerated for example by hydrolysis in the presence of an acid (e.g. hydrochloric or acetic) at a temperature of 0°–100°C.

The following Examples are given by way of illustration only.

All temperatures are in degress Celsius. Ultra violet spectra were measured in ethanol. Optical rotations were measured in chloroform at approximately 1% w/v concentration unless stated otherwise. 'Petrol' refers to petroleum ether (b.p. 60-80°). Preparative thin layer chromatography ('preparative t.l.c.') was carried out on silica gel.

EXAMPLES 1–20

A number of 3α-hydroxy-5α-pregnane-11,20-diones (one of which was a 19-nor compound) and one 3α-hydroxy-5α-pregnan-20-one were prepared, all the compounds having the group R CO.S- at the 21-position. The compounds were prepared by the method described below, and variations in the method and some properties of the compounds are shown in Table I.

Preparation of thioesters of Table I

A solution of 21-bromo-3α-hydroxy-5α-pregnane-11,20-dione (1.0 g.) in dry acetone (30 ml.) was treated with an aminothioacid or the sodium salt of a thioacid (0.7 g.) and the resulting mixture refluxed. The solution was then evaporated under reduced pressure and the residue was partitioned between water and ether. The organic layer was washed with water, dried ($Na_2SO_4$) and evaporated. The residue was purified by preparative t.l.c. and/or recrystallisation. Physical properties and yields are summarised in the table.

TABLE 1

| Ex. No. | R | Eluting Solvent | Recrystallising Solvent | Yield mg. | M.pt. °C | $[\alpha]_D$ | c | Reaction Time (mins.) |
|---|---|---|---|---|---|---|---|---|
| 1 |  | — | — | 410 | — | +100° | 1.0 | 40 |
| 2 |  | — | — | 450 | — | + 82° | 1.0 | 40 |
| 3 |  | — | — | 650 | — | +106° | 1.0 | 40 |
| 4 |  | — | — | 300 | — | + 93° | 1.0 | 40 |
| 5 |  | A/P | | 300 | 187 | +113° | 1.0 | 40 |
| 6 |  | EA/P | | 450 | 198–9 | +115° | 1.0 | 40 |
| 7 | 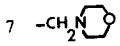 | A/P | | 360 | 157–8 | +104° | 1.0 | 40 |
| 8 |  | A/P | | 31 | 185–90 | — | — | 40 |
| 9(1) | —$CH_3$ | MA/P | | 600 | 184–5 | +108 | 1.0 | 30 |

TABLE 1-continued

| Ex. No. | R | Eluting Solvent | Recrystallising Solvent | Yield mg. | M.pt. °C | $[\alpha]_D$ | c | Reaction Time (mins.) |
|---|---|---|---|---|---|---|---|---|
|  |  |  |  |  | (dec.) |  |  |  |
| 10(6,2) | -CH$_2$-N(pyrrolyl) | EA/P 1:1 | — | 172 | — | +103° | 1.1 | 30 |
| 11(8) | —CH$_2$CH$_2$CH$_3$ | EA/C | — | 250 | — | +122° | 1.2 | 60 |
| 12(3,6) | —(CH$_2$)$_3$CH$_3$ | EA/P 1:1 | — | 560 | — | +110° | 0.9 | 90 |
| 13(1) | —CH$_3$ | C | A/P | 500 | 165 | +118° | 1.0 | 30 |
| 14(1,4) | —CH$_3$ | C | A/P | 400 | 157–9 | +109° | 0.8 | 90 |
| 15(5) | -CH$_2$-N(pyrrolyl) | EA/C | MA/P | 300 | 180–1 | + 94° | 1.2 | 30 |
| 16(4) | furyl-SMe | C | A/P | 200 | — | +112° | 1.0 | 30 |
| 17 | -CH(CH$_2$CH$_2$CH$_3$)-N(pyrrolyl) | EA/C 1:1 | — | 700 | — | + 95° | 1.7 | 30 |
| 18(4,6,7) | -CH$_2$-N(pyrrolyl) | EA/P 1:1 | A/P | 110 | 190–2 (dec.) | +160° | 0.78 | 50 |
| 19 | -CH$_2$-N(pyrrolyl) | EA/C 1:1 | — | 400 | — | + 74° | 1.2 | 30 |
| 20 | -CH$_2$-N(pyrrolyl) | EA/C | — | 400 | — | + 85° | 0.9 | 30 |

Notes to Table I

1. The potassium salt was used.
2. Proportions used - 21-bromo compound (240 mg.), thioacid (120 mg.), acetone (40 ml.).
3. Proportions used - 21-bromo compound (750 mg.), salt of thioacid (1.5 gm.), acetone (40 ml.).
4. 50 ml. of acetone were used.
5. Proportions used - 21-bromo (0.7 gm.), thioacid (0.5 gm.).
6. Extracting solvent was ethylacetate.
7. Proportions used - 21-bromo compound (0.5 gm.), thioacid (0.3 gm.).
8. 1.0 gm. of thioacid as its salt were used.

The compound of Example 10 possesses a 2β-methyl substituent.

The compounds of Example 13 and 14 possess a 2β-methoxy substituent.

The compound of Example 15 possesses a 3β-methyl group.

The compound of Example 18 is a 19-norpregnane.

The compound of Example 19 possesses a 2β-ethoxy substituent.

The compound of Example 20 possesses a double bond at the 1,2-position.

All the steroids are 11-ketones with the exception of the compound of Example 14, which is an 11-desoxy compound.

A = acetone
P = petrol
C = chloroform
EA = ethyl acetate
MA = methyl acetate
dec. = decomposition.

The column headed c indicates the concentration (% w/v) at which the optical rotation was measured.

EXAMPLE 21

21-Ethylthio-3α-hydroxy-5α-pregnane-11,20-dione

Ethanethiol (5.0 ml.) was added to a warm (40°) solution of sodium (3.0 g.) in a mixture of propan-2-ol (125 ml.) and toluene (150 ml.). 21-Bromo-3α-hydroxy-5α-pregnane-11,20-dione (3.5 g.) was then added and the resulting mixture was allowed to cool to room temperature over 30 min. The mixture was then partitioned between water and ether and the organic layer was washed with water, dried (Na$_2$SO$_4$) and evaporated. The residue was subjected to preparative t.l.c. (EtOAc/petrol, 1:10).

The most polar component was identified as the title compound (0.5 g.) and was obtained as a white foam $[\alpha]_D$ + 93° (C 1.2).

EXAMPLE 22

21-Ethylsulphonyl-3α-hydroxy-5α-pregnane-11,20-dione

A solution of a mixture of R- and S-21-ethylsulphinyl-3α-hydroxy-5α-pregnane-11,20-dione (0.3 g) in dry methylene chloride (10 ml.) was treated with m-chloroperoxybenzoic acid (0.3 g.) at room temperature for 1 hr. and then partitioned between dilute aqueous sodium bicarbonate and methylene chloride. The organic layer was washed with water, dried (Na$_2$SO$_4$) and evaporated. The residue was purified by preparative t.l.c. (CHCl$_3$) to give title compound (0.15 g.), as a white foam; $[\alpha]_D$ + 109° (c 1.4).

EXAMPLE 23

3α-Hydroxy-21-isopropylthio-5α-pregnane-11,20-dione

Propane-2-thiol (1.3 ml.) was added to a warm solution of sodium (0.6 g.) in a mixture of propan-2-ol (25 ml.) and toluene (30 ml.). 21-Bromo-3α-hydroxy-5α-pregnane-11,20-dione (0.7 g.) was then added and the mixture was gently refluxed for 2 hr. The mixture was then partitioned between water and ether and the organic layer was washed with water, dried ($Na_2SO_4$) and evaporated. The residual foam was purified by preparative t.l.c. ($CHCl_3$) to give title compound (0.2 g.) as a white foam, $[\alpha]_D + 67°$ (c 1.3).

EXAMPLE 24

21-Benzylthio-3α-hydroxy-5α-pregnane-11,20-dione

Toluene-α-thiol (1.0 ml.) was added to a warm solution of sodium (0.6 g.) in a mixture of propan-2-ol (25 ml.) and toluene (30 ml.). 21-Bromo-3α-hydroxy-5α-pregnane-11,20-dione (0.7 g.) was then added and the mixture was gently refluxed for 2 hr. The mixture was then partitioned between water and ether and the organic layer was washed with water, dried ($Na_2SO_4$) and evaporated. The residue was purified by preparative t.l.c. ($CHCl_3$) to give title compound (0.4 g.) as a white foam, $[\alpha]_D + 89°$ (c 1.1).

EXAMPLE 25

3α-Hydroxy-21-thiocyanato-5α-pregnane-11,20-dione

A solution of 21-bromo-3α-hydroxy-5α-pregnane-11,20-dione (0.75 g.) in acetone (50 ml.) was treated with a solution of barium thiocyanate (2.6 g.) in water (10 ml.). The resulting mixture was refluxed for 4 hr., cooled and then partitioned between water and ether. The organic layer was washed with water, dried ($Na_2SO_4$) and evaporated. The residue (720 mg.) was purified by preparative t.l.c. (EtOAc) to afford title compound (685 mg.) as a white foam, $[\alpha]_D + 67°$.

EXAMPLE 26

3α-Hydroxy-21-[2'-morpholinoethylthio]-5α-pregnane-11,20-dione

2-Morpholinoethanethiol (1 ml.) was added to a warm solution of sodium (0.6 g.) in a mixture of dry toluene (30 ml.) and isopropyl alcohol (25 ml.). After 5 min., 21-bromo-3α-hydroxy-5α-pregnane-11,20-dione (2.0 g.) was added and the resulting mixture was stirred at 40° for 30 min. The mixture was then partitioned between water and ether and the organic layer was washed with water, dried ($Na_2SO_4$) and evaporated. The residue was subjected to preparative t.l.c. (EtOAc) to give title compound (150 mg.) as a white foam, $[\alpha]_D + 73°$ (c 0.9); $\lambda_{max.}$ 243 nm. ($\epsilon$ 570).

EXAMPLE 27

3α-Hydroxy-21-morpholinoethoxythiocarbonylthio-5α-pregnane-11,20-dione

A mixture of morpholinoethanol (3.3 g., 2.5 mmole), dry toluene (50 ml.) and sodium (0.6 g.) was refluxed under nitrogen for 6 hr. and then left at room temperature for two days. The unreacted sodium was then removed and carbon disulphide (4 ml., 5.3 mmole) was added cautiously and the resulting mixture was allowed to stand at room temperature for 2 hr. The precipitated solid was collected rapidly by filtration and added immediately to a solution of 21-bromo-3α-hydroxy-5α-pregnane-11,20-dione (1.0 g., 2.3 mmole) in acetone. The resulting suspension was refluxed for 15 min. and then partitioned between water and ether. The organic layer was washed with water, dried ($Na_2SO_4$) and evaporated. The residue (900 mg.) was purified by preparative t.l.c. (EtOAc/petrol 1:1) to give title compound (0.35 g.) as a white foam, $[\alpha]_D + 77°$ (c 1.2).

EXAMPLE 28

3α-Hydroxy-21-morpholinoethoxythiocarbonylthio-5α-pregnane-11,20-dione citrate

A solution of 3α-hydroxy-21-morpholinoethoxythio carbonyl thio-5α-pregnane-11,20-dione (80.664 mg; 0.15 mmole) in aqueous ethyl alcohol (2 ml.), was treated with an aqueous solution of citric acid (0.1 M; 1.5 ml.), and the resultant suspension was evaporated to dryness in vacuo. The residue was suspended in water. The solution was partially decanted, and centrifuged. The cloudy supernatant solution was removed (1.6 ml.). The insoluble material was recovered (64 mg.) Hence it was assumed the amount of steroidal citrate formed utilised. 16.5 mg. of steroid and the cloudy solution (1.6 ml) contains 10 mgs/ml of title compound.

EXAMPLE 29

3α-Hydroxy-21-(4'-morpholinocarbodithio)-5α-pregnane-11,20dione

A mixture of 21-bromo-3α-hydroxy-5α-pregnane-11,20-dione (1.0 g.), morpholinocarbodithioic acid sodium salt (0.8 g.) and acetone (30 ml.) was refluxed for 15 min. and then evaporated to dryness. The residue was partitioned between ether and water and the organic layer was washed with water, dried ($Na_2SO_4$) and evaporated. The residue was subjected to preparative t.l.c. (EtOAc/$CHCl_3$ 1:1) to give title compound (0.3 g.) as a white foam, $[\alpha]_D + 110°$ (c 1.1).

Example 30

R- and S-21-Ethylsulphinyl-3α-hydroxy-5α-pregnane-11,20-dione

A solution of 21-ethylthio-3α-hydroxy-5α-pregnane-11,20-dione (0.3 g.) in dry methylene chloride (10 ml.) was cooled to 0° and treated with m-chloroperbenzoic acid (0.15 g.). The resulting solution was stirred at 0° for 30 min. and partitioned between dilute aqueous sodium bicarbonate and methylene chloride. The organic layer was washed with water, dried ($Na_2SO_4$) and evaporated. The residue was subjected to preparative t.l.c. (EtOAc/($CH_3$)$_2$CO 1:1) to give a 1:1 mixture of R- and S-21-Ethylsulphinyl-3α-hydroxy-5α-pregnane-11,20-dione (0.17 g.) as a white foam, $[\alpha]_D + 44°$ (c 1.2).

Example 31

2β-Ethoxy-3α-hydroxy-21-mercapto-5α-pregnane-11,20-dione

A 1% aqueous solution of 2β-ethoxy-3α-hydroxy-21-morpholinoacetylthio-5α-pregnane-11,20-dione hydrochloride was allowed to stand at room temperature for four weeks. The precipitated solid was collected by filtration, washed with water and dried in vacuo to give the title compound, m.p. 112°–18° (dec.); $[\alpha]_D + 160°$ (c 0.5).

EXAMPLE 32

3α-Hydroxy-21-thiamorpholinoacetylthio-5α-pregnane-11,20-dione

21-Bromo-3α-hydroxy-5α-pregnane-11,20-dione (500 mg.) 4-thiamorpholinothioacetic acid (400 mg.)

in dry actone (40 ml.) was heated on a steam bath for 10 minutes. Acetone was removed (red. pressure) and the residue was partitioned between ethyl acetate and water. The aqueous layer was re-extracted with ethyl acetate and the combined organic layers were washed with water, dried (MgSO$_4$) and evaporated. The crude product was purified by preparative T.L.C. (ethyl acetate:petrol, 3:5). The main band afforded the title compound (378 mg.) as a white foam $[\alpha]_D + 97°$ c 0.92; $\lambda_{max}$. 231.5 nm (2,890).

EXAMPLE 33

21-Morpholinoacetylthio-3α-hydroxy-5α-pregnane-11,20-dione citrate

A mixture of 21-morpholinoacetylthio-3α-hydroxy-5α-pregnane-11,20-dione (245.8 mg., 0.5 mmole) and 0.1 M aqueous citric acid (10 ml., 1.0 mmole) was shaken vigorously for 30 minutes. The undissolved solid (138 mg.) was removed by filtration and the filtrate was assumed to contain 107 mg. of free steroidal base as its citrate in 10 ml. of solution. The filtrate was therefore an approximately 1% aqueous solution of the title compound.

EXAMPLE 34

21-nButyltrithiocarbonato-3α-hydroxy-5α-pregnane-11,20-dione

21-Bromo-3α-hydroxy-5α-pregnane-11,20-dione (1.0 g.) potassium nbutyltrithiocarbonate (500 mg.) was refluxed in dry acetone for 4½ hours.

The mixture was then partitioned between ethyl acetate and water. The organic layer was separated, washed with water, dried (MgSO$_4$) and evaporated. The residue was purified by preparative T.L.C. (CHCl$_3$) the main band was removed and purified further by preparative T.L.C. (ethylacetate:petrol 1:2) and the intense yellow band (rf ≃ 0.5) was removed to give title compound (300 mg.) as a bright yellow foam $[\alpha]_D + 98$ $\lambda_{max}$. 222 nm $\epsilon$ 6,000), 308 nm $\epsilon$ 15,000).

EXAMPLE 35

21-Morpholinoacetylthio-3α-hydroxy-5α-pregn-1-ene-11,20-dione hydrochloride

21-Morpholinoacetylthio-3α-hydroxy-5α-pregn-1-ene-11,20-dione (122 mg., 0.25 mmole) was dissolved in 0.1 M hydrochloric acid (2.5 ml.) and the resulting clear solution was made up to 12 ml. by the addition of distilled water to give a 1% aqueous solution of the title compound.

EXAMPLE 36

3α-Hydroxy-21-1', 2', 5', 6'-tetrahydropyridinoacetylthio-5α-pregnane-11,21-dione 21-Bromo-3α-hydroxy-5α-pregnane-11,20-dione (200 mg.), freshly purified, in dry acetone (40 ml.) and 1,2,5,6-tetrahydropyridinylthioacetic acid (100 mg.) m.p. 180° exH$_2$O was heated on a steam bath for 10 minutes. The reaction mixture was concentrated (< 20' in vacuo) and the residue was partitioned between ether and water. The aqueous layer was reextracted with ether and the combined ether extract was washed with water, dried (Na$_2$SO$_4$) and evaporated to giave the title compound (160mg) as a white foam $[\alpha]_D + 65°$ (c. 0.40)$\lambda_{max}$. 222 nm ($\epsilon$ 4,200) 226.5 nm ($\epsilon$ 4,100).

EXAMPLE 37

2β-Ethoxy-21-morpholinoacetylthio-3α-hydroxy-5α-pregnane-11,20-dione hydrochloride 2β-Ethoxy-3α-hydroxy-21-morpholinoacetylthio-5α-pregnane-11,20-dione (134 mg., 0.25 mmole) was dissolved in 0.1 M hydrochloric acid (2.5 ml. 0.25 mmole) and the resulting clear solution was diluted to 13 ml. by the addition of distilled water to give a 1% aqueous solution of the title compound.

EXAMPLE 38

3α-Hydroxy-21-morpholinoacethylthio-5α-pregnane-11,20-dione hydrochloride

A suspension of 3α-hydroxy-21-morpholinoacetylthio-5α-pregnane-11,20-dione (245.8 mg., 0.5 mmole) in 0.1 N hydrochloric acid (10 ml., 1.0 mmole) was shaken at room temperature for 30 minutes.

The undissolved base (45 mg.) was collected by filtration and washed with water (1 ml.) and the filtrate and washings were combined and diluted with water (9 ml.) to give an aqueous solution of the title compound.

EXAMPLE 39

21-(3-chloro-n-propionylthio)-3α-hydroxy-5α-pregnane-11,20-dione

A solution of 21-morpholinoacetylthio-5α-pregnane-3,11,20-trione (160 mg.,) in a mixture of ethanol (8 ml) and 2N-hydrochloric acid (20 ml) was heated on a steam bath for 6 hrs., cooled and partitioned between water and ether. The organic layer was washed with water, dried (Na$_2$SO$_4$) and evaporated. The residue was subjected to preparative t.l.c. and the major product isolated. N.m.r showed it to be 21-mercapto-5α-pregnane-3,11,20-trione.

A mixture of chloropropionyl chloride (32 mg.) and pyridine (20 mg.) in dry tetrahydrofuran (3 ml) was added to a solution of the above trione (90 mg.) in dry tetrahydrofuran and the resulting mixture was left at room temperature for 30 min., and then partitioned between water and ether. The organic layer was washed with water, dried (Na$_2$SO$_4$) and evaporated. The residue was subjected to preparative t.l.c. (EtOAC/CHCl$_3$ 1:4) to give 21-(3-chloro-n-propionylthio)-5α-pregnane-3,11,20-trione.

A solution of this trione (60 mg.) in "stock" chloroiridic acid solution (5 ml) was refluxed for 1 hr., cooled and partitioned between water and ether. The organic layer was washed with water, dried (Na$_2$SO$_4$) and evaporated. This residue was subjected to preparative t.l.c. (EtOAC/CHCl$_3$ 1:1) to give title compound (45 mg.) overall yield as a white foam $[\alpha]_D + 124°$.

EXAMPLE 40

3α-Hydroxy-21-(pyrid-2ylthio)-5α-pregnane-11,20-dione

A solution of 21-bromo-3α-hydroxy-5α-pregnane-11,20-dione (1.0 g.) in tetrahydrofuran (10 ml) was added to a solution of pyrid-2-thione (0.5 g) in 2N-aqueous sodium hydroxide (10 ml). After allowing the mixture to stand at room temperature for 3 mins., water and ether were added. The organic layer was washed with water, dried (Na$_2$SO$_4$) and evaporated. The residue was subjected to preparative t.l.c. and recrystallisation from methyl acetate/petrol to give title compound (240 mg.) as white needles m.p. 184° [α]$_D$ + 130° (c 0.9).

EXAMPLE 41

3α-Hydroxy-21-(3'-morpholino-n-propionylthio)-5α-pregnane-11,20-dione

A mixture of 21-(3-chloro-n-propionylthio)-3α-hydroxy-5α-pregnane-11,20-dione (200 mg.), dry tetrahydrofuran (10 ml.) and morpholine (100 mg.) was refluxed for 24 hr. The mixture was partitioned between ethyl acetate and water and the organic layer was washed with water, dried (Na$_2$SO$_4$) and evaporated. The residue was subjected to preparative layer chromatography (EtOAc:CHCl$_3$) to give title compound (120 mg.) as a foam; [α]$_D$ + 94°.

EXAMPLE 42

3α-Hydroxy-21-(4'-morpholino-n-butyrylthio)-5α-pregnane-11,20-dione

A solution of 21-morpholinoacetylthio-5α-pregnane-3,11,20-trione (480 mg.) in a mixture of ethanol (28 ml.) and 2N-hydrochloric acid (60 ml.) was heated on a steam bath for 6 hr., cooled and partitioned between water and ether. The organic layer was washed with water, dried (Na$_2$SO$_4$) and evaporated. The residual 21-thiol was purified by preparative t.l.c.

A solution of the product in dry pyridine (2 ml.) was treated at 0' with a mixture of 4-chloro-n-butyryl chloride (90 mg.), pyridine (60 mg.) and dry tetrahydrofuran (10 ml.). The resulting mixture was left at room temperature for 30 min. and partitioned between ethyl acetate and water. The organic layer was washed with water, dried (Na$_2$SO$_4$) and evaporated. 21-(4'λ chlorobutyrylthio)-5α-pregnane-3,11,20-trione.

A solution of the trione in "stock" chloroiridic acid (15 ml; see Preparation 7) was refluxed for 4 hours, cooled and partitioned between water and ether. The organic layer was washed with water, dried (Na$_2$SO$_4$) and evaporated. The residue was purified by preparative t.l.c. (EtOAc:CHCl$_3$) to give 3α-hydroxy-21-(4'-chlorobutyrylthio)-5α-pregnane-11,20-dione.

A mixture of the dione, dry tetrahydrofuran (15 ml.) and morpholine (0.2 ml.) was refluxed for 24 hr. The mixture was then partitioned between ethyl acetate and water and the organic layer was washed with water, dried (Na$_2$SO$_4$) and evaporated. The residue was subjected to preparative t.l.c. (EtOAc : CHCl$_3$) to give the title compound (84 mg.) as a foam [α]$_D$ + 90° (c 0.8).

EXAMPLE 43

3α-Hydroxy-21-(pyrid-2'-ylthio)-5α-pregnane-11,20-dione

21-Bromo-3α-hydroxy-5α-pregnane-11,20-dione (1g) in dry tetrahydrofuran (12 ml) was treated with 2-mercaptopyridine (0.5g) in 2N-aqueous sodium hydroxide (10 ml). The mixture was left at room temperature for 45 minutes, partitioned between ether and water and the organic layer was washed with water, dried and evaporated. The crude residue was purified by preparative T.L.C. and the product crystallised from ether to give the title compound (210 mg) m.p. 127°–130°C [α]$_D$+128°.

Formulations

EXAMPLE A dissolved 0.106 g. of 3α-hydroxy-21-thiocyanato-5α-pregnane-11,20-dione were dissoled in 2 ml. of acetone at 20°C. The resulting solution was added to 2 g. of Cremophor EL at 20°C and stirred until homogeneous. The acetone was removed by a vigorous stream of nitrogen. The solution was diluted with sterile distilled water containing 0.05 g. of sodium chloride to give a final volume of 10 ml.

EXAMPLE B 0.01 g. of 21-acetylthio-3α-hydroxy-5α-pregnane-11,20-dione were dissolved in 2 ml. of acetone at 20°C. The resultng solution was added to 1 g. of Cremophor EL at 20°C and stirred until homogeneous. The acetone was removed by a vigorous stream of nitrogen. The solution was diluted with sterile distilled water containing 0.025 g. of sodium chloride to give a final volume of 5 ml.

EXAMPLE C 0.021 g. of 3α-hydroxy-21-morpholino-acetylthio-5α-pregnane-11,20-dione were dissolved in 2 ml. of acetone at 20°C. The resulting solution was added to 2 g. of Cremophor EL at 20°C and stirred until homogeneous. The acetone was removed by a vigorous stream of nitrogen. The solution was diluted with sterile distilled water containing 0.05 g. of sodium chloride to give a final volume of 10 ml.

EXAMPLE D 0.025g of 21-acetyl-thio-3α-hydroxy-5β-pregnane-11,20dione are dissolved in 2ml of acetone at 20°C. The resulting solution is added to 2g of Cremophor El at 20°C and stirred until homogeneous. The acetone is removed by a vigorous stream of nitrogen. The solution is diluted with sterile distilled water containing 0.05g of sodium chloride to give a final volume of 10ml.

PREPARATIONS

Preparation 1

21-Bromo-3α-hydroxy-5α-pregnane-11,20-dione

A stirred solution of 2β-bromo-3α-hydroxy-5α-pregane-11,20-dione (5.0 g.) in methanol (100 ml.) was treated at 0° with a solution of bromine (1 ml.) in methanol (30 ml.) at such a rate that the yellow colour disappeared before further addition of the bromine solution. The mixture was then poured into water and the precipitated solid was collected by filtration, washed with water and dried over P$_2$O$_5$ in vacuo. The resulting solid (5.0 g.) was purified by column chromatography (silica, EtOAc/C$_6$H$_6$, 1:2.5) to give crude 2β,21-dibromo-3α-hydroxy-5α-pregnane-11,20-dione (3.4 g.).

A solution of crude 2β,21-dibromo-steroid (2.0 g.) in benzene (100 ml.) was treated with dihydropyran (2 ml.) and p-toluenesulphonic acid (40 mg.) for 20 minutes. The reaction mixture was then washed successively with dilute aqueous sodium bicarbonate and water, dried (Na$_2$SO$_4$) and evaporated. The residue was subjected to preparative tlc (CHCl$_3$) to give slightly crude 2β, 21-dibromo-3α-tetrahydropyranoxy-5α-pregnane-11,20-dione as a white foam.

A mixture of this product (0.7 g.), dimethylacetamide (20 ml.), lithium bromide (2.6 g.) and calcium carbonate (4.0 g.) was stirred at 100° for 2 hour. The calcium carbonate was then removed by filtration and the filtrate was partitioned between ether and water. The organic layer was washed with water, dried ($Na_2SO_4$) and evaporated.

A solution of the residue (0.5 g.) in ethanol (5 ml.) was stirred at room temperature with 2N-hydrochloric acid (0.5 ml.) for 2 hours. The mixture was then partitioned between aqueous sodium bicarbonate and ether. The orgainc layer was washed with water, dried ($Na_2SO_4$) and evaporated. The residue was subjected to preparative tlc (EtOAc/$CHCl_3$, 1:2) to give title compound (0.15 g.) as a white foam, $[\alpha]_D + 85°$ (c 0.8).

Preparation 2

4-Morpholinothioacetic acid

A cold solution of sodium hydroxide (3.6 g.) in water (10 ml.) was added to a solution of chloroacetic acid (8.5 g.) in water (10 ml.) with external cooling. Morpholine (7.85 g.) was added and the resulting mixture was left at room temperature for 20 min, and then refluxed for 20 min. The solution was then evaporated to dryness and ethanol (75 ml.) was added. The precipitated sodium chloride was removed by filtration and the filtrate was evaporated. A solution of barium hydroxide (25 g.) in water (70 ml.) was added and the solution was evaporated in vacuo. The residue was repeatedly treated with water and evaporated between each treatment. The final residue was dissolved in hot water (100 ml.), carbon dioxide was bubbled through the mixture and filtered. The filtrate was evaporated and the residue was dissolved in hot ethanol, filtered again and the filtrate was evaporated to give barium 4-morpholinoacetate (18 g.). The solid was treated with 2N-sulphuric acid and filtered. Evaporation of the filtrate gave crude morpholinoacetic acid as a gum which crystallised to a powdery solid after leaving over $P_2O_5$ in vacuo.

A mixture of morpholinoacetic acid (7.25 g.), redistilled triethylamine (7.0 ml.) and methylene chloride (100 ml.) was cooled to 0° and treated with redistilled ethyl chloroformate (5.25 ml.). A further quantity of redistilled triethylamine (7.0 ml.) was added and the mixture was then cooled to −20°. Hydrogen sulphide was then passed through the stirred mixture for 15 min, and the solution was then allowed to warm to room temperature. Excess hydrogen sulphide was removed in vacuo and concentrated hydrochloric acid (5 ml.) was added. Methylene chloride was removed in vacuo and the residue was treated with water (70 ml.). On cooling the solution to 0°, buff needles separated and were collected by filtration to give title compound (0.5 g.), m.p. 165°–7°.

Preparation 3

21-Bromo-3α-hydroxy-19-nor-5α-pregnane-11,20-dione

A solution of 3α-hydroxy-19-nor-5α-pregnane-11,20-dione (5.0 g.) in dry methanol (300 ml.) was stirred at 0°–5° during the dropwise addition of bromine (0.82 ml.) in methanol (20 ml.). After 1 hour the reaction was extremely slow (as indicated by removal of bromine colouration before further addition). External cooling was removed and hydrobromic acid (1 drop) was added. Further addition of bromine resulted in rapid decolouration and the reaction was completed in a further 1.5 hours. The reaction mixture was partitioned between ethyl acetate and water, washed with water, dried ($MgSO_4$) and evaporated to give a white foam (6.2 g.). Isolation of the main band after preparative t.l.c. (EtOAc) gave 90% pure title compound (5.2 g.).

Preparation 4

11α-Hydroxy-19-norpregna-4,16-diene-3,20-dione

A solution of a mixture of 11α,17α-dihydroxy-19-norpregn-4-ene-3,20-dione (4 g.) and semicarbazide hydrochloride (4 g.) in methanol (200 ml.) was refluxed for 2 hr. The methanol was then removed by distillation under reduced pressure and water was added to the residue. The precipitated solid was collected by filtration, washed with water and dried over $P_2O_5$ in vacuo. A solution of this solid in a mixture of glacial acetic acid (80 ml.) water (28 ml.) and pyruvic acid (4 ml.) was heated on a steam bath for 1 hr. The resulting solution was concentrated under reduced pressure and partitioned between saturated aqueous sodium bicarbonate and ethyl acetate. The organic layer was washed with water, dried ($Na_2SO_4$) an evaporated to dryness. The residue was subjected to preparative t.l.c. ($CHCl_3$, ($CH_3$)$_2$ CO; 15 : 1) and crystallised from acetone/petrol to afford title compound (1.6 g.) as white needles, m.p. 149°.

Preparation 5

19-nor-5α-pregna-3,11,20-trione via 3ξ,11α,20ξtrihydroxy-19-nor-5α-pregnane

A solution of 11α-hydroxy-19-norpregna-4,16-diene-3,20-dione (2.5 g.) in dry tetrahydrofuran (200 ml.) was added over 5 mins. to a solution of lithium (5 g.) in liquid ammonia (2.5 liters). The solution was then left for 30 min. Ethanol (ca. 100 ml.) was then added until the blue colour had been discharged and the ammonia was then allowed to evaporate. The residue was partitioned between water and ether. The organic layer was washed, dried ($Na_2SO_4$) and evaporated to give crude title compound (1.5 g.)

Preparation 6

19-Nor-5α-pregnane-3,11,20-trione

A solution of crude 3ξ,11α,20ξ-trihydroxy-19-nor-5α-pregnane (4 g.) in acetone (280 ml.) was treated with a solution of potassium dichromate (8.0 g.) in 2N-sulphuric acid (38 ml.) at room temperature for 1 hr. An additional quantity of potassium dichromate (8 g.) in 2N-sulphuric acid (38 ml.) was then added and left at room temperature for 15 mins. The solution was then partitioned between water and ether and the organic layer was washed with water, dried ($Na_2SO_4$) and evaporated. The residual oil was subjected to preparative t.l.c. ($CHCl_3$) and recrystallised from acetone/petrol to afford title compound (1.04 g.) as white prisms, m.p. 151°, $[\alpha]_D + 240°$.

Preparation 7

3α-Hydroxy-19-nor-5α-pregnane-11,20-dione

A solution of 19-nor-5α-pregnane-3,11,20-trione (0.9 g.) in "stock" chloroiridic solution [prepared by refluxing a mixture of chloroiridic acid (0.09 g.) 90% isopropyl alcohol (200 ml.) and trimethyl phosphite (16 ml.) for 16 hr. The solution was neutralised with triethylamine immediately prior to use] (75 ml.) was refluxed for 24 hr. The solution was then cooled, partitioned between water and ether and the organic layer was washed well with water, dried (Na$_2$SO$_4$) and evaporated. The residue was subjected to preparative t.l.c. (EtOH) and recrystallized from acetone to afford title compound (0.6 g.) as white needles, m.p. 154°, $[\alpha]_D$ + 200°.

Preparation 8

21-Bromo-3α-hydroxy-3β-methyl-5α-pregnane-11,20-dione

A stirred solution of 3α-hydroxy-3β-methyl-5α-pregnane-11,20-dione (5.0 g., 15.0 mmole) in methanol (300 ml.) was treated with a solution of bromine (1.0 ml.) in methanol (30 ml.) at 0° and at such a rate that the yellow colour of the solution disappeared before further addition of the bromine solution took place. The mixture was then poured into water, the precipitated title compound (2.8 g.) was collected by filtration and dried over P$_2$O$_5$ in vacuo.

Preparation 9

21-Bromo-3α-hydroxy-2β-methoxy-5α-pregnane-11,20-dione

A solution of 3α-hydroxy-2β-methoxy-5α-pregnane-11,20-dione (2 g.) in methanol (15 ml.) was treated with hydrobromic acid in glacial acetic acid (3 drops). The mixture was stirred at room temperature and bromine (530 mg.) in methanol (1.45 ml.) was added dropwise over a period of 30 minutes. The mixture was stirred for a further 30 minutes and poured into water, stirred, filtered, washed with water and dried. Purification by preparative t.l.c., followed by crystallisation from ethyl acetate and petrol gave title compound (250 mg.) as colourless plates; m.p. 185°–188°; $[\alpha]_D$ + 104°.

Preparation 10

Piperidinothioacetic Acid

A solution of monochloroacetic acid (9.35 g.) in water (40 ml.) was adjusted to pH 8.0 with a solution of sodium hydroxide (4.0 g.) in water (30 ml.). Piperidine (8.0 ml.) was then added and the mixture was left at room temperature for 2 days and then heated on a steam bath for 2 hr. The solution was then evaporated and the residue was digested with hot ethanol, filtered and the filtrate was evaporated to give piperidinoacetic acid (12.55 g.) as a brown glass.

A solution of piperidinoacetic acid (7.45 g.) and redistilled triethylamine (7.0 ml.) in methylene chloride (100 ml.) was cooled at 0° and treated dropwise with redistilled ethyl chloroformate (5.25 ml). A further quantity of triethylamine (7.0 ml.) was added and the solution was cooled to −20°. Hydrogen sulphide was then passed through the solution for 15 min. and the resulting mixture was allowed to warm to room temperature. Excess hydrogen sulphide was then removed in vacuum and concentrated hydrochloric acid (5 ml.) was added. The methylene chloride was removed in vacuo and water (50 ml.) was added. On cooling the solution to 0° white plates were deposited which were collected by filtration to give title compound (0.7 g.) of m.p. 185°–7°.

Preparation 11

2-Morpholino-n-thiovaleric acid

A cold solution of sodium hydroxide (3.6 g.) in water (10 ml.) was added to a solution of 2-bromo-n-valeric acid (16 ml.) in water (10 ml.) with external cooling. Morpholine (7.9 g.) was added and the resulting mixture was left at room temperature for 20 minutes and then refluxed for 30 minutes. The solution was then evaporated to dryness and ethanol (75 ml.) was added. The precipitated sodium chloride was removed by filtration and the filtrate was evaporated. A solution of barium hydroxide (25 g.) in water (70 ml.) was added and the solution was evaporated in vacuo. The residue was repeatedly treated with water and evaporated between each treatment. The final residue was dissolved in hot water and carbon dioxide was bubbled through the solution and the precipitate was removed by filtration. The filtrate was evaporated and the residue was dissolved in ethanol, filtered again and the filtrate was evaporated. The residual solid was treated with 2N-sulphuric acid and centrifuged. The clear solution was decanted from the solid and it was evaporated to give a gum which was dried in vacuo over P$_2$O$_5$.

The gum was treated with redistilled triethylamine (7.0 ml.) and methylene chloride (100 ml.) at 0°. The mixture was then treated with redistilled ethyl chloroformate (5.25 ml.). A further quantity of triethylamine (7.0 ml.) was added and the mixture was then cooled to −20°. Hydrogen sulphide was then passed through the stirred mixture for 15 minutes and the solution was then allowed to warm to room temperature. Excess hydrogen sulphide was removed in vacuo and concentrated hydrochloric acid (5 ml.) was added. Methylene chloride was then removed in vacuo and the residue was recrystallised from hot water to give the title compound (8.0 g.) as white plates, m.p. 180° (dec.).

Preparation 12

4-Thiamorpholino acetic acid 1,4-Thiamorpholine (5.2 g.) was added to a solution of chloroacetic acid (4.73 g.) in water (5 ml.) neutralised with cooling with sodium hydroxide (2.0 g.) in water (5 ml.).

After crystallisation had set in (pH of solution 7) the reaction mixture was refrigerated overnight. The crystalline solid was removed by filtration and dried (80° high vac. 2 hours) to give the title compound (1.9 g.) as buff plates m.p. >250° dec.

The filtrate was evaporated to dryness, residue triturated with absolute ethanol (50 ml.) insoluble material (NaCl) was removed by filtration, and the filtrate was evaporated. Barium hydroxide (14 g.) in hot water (40 ml.) was added and the mixture evaporated in vacuo with repeated addition of water (6 × 50 ml.). The residue was dissolved in hot water (100 ml.), saturated with carbon dioxide and filtered. Evaporation of the filtrate gave an orange foam which was redissolved in water (100 ml.) and acidified to pH 3 (2NH$_2$SO$_4$).

The insoluble inorganic material was removed by centrifuging and the supernatant liquid evaporated to a dark brown gum, which after trituration with hot absolute ethanol (150 ml.) gave after drying (high vac; 60°) 4-thiamorpholino acetic acid (3.4 g; 42%) as a slightly hygroscopic pink powder m.p. >250°dec.

Preparation 13

4-Thiamorpholinothioacetic acid

4-Thiamorpholino acetic acid (1.61 g.), triethylamine (1.4 ml.) was stirred in dry methylene chloride (15 ml.) at 0° during dropwise addition of ethyl chloroformate (1.2 ml.).

The reaction mixture was stirred for 1 hour at 0°–10° and triethylamine (1.4 ml.) was added. The suspension was then cooled to −20° and saturated with hydrogen sulphide for 15 minutes and left to warm to room temperature. Excess hydrogen sulphide was removed in vacuo and concentrated hydrochloric acid (1 ml.) was added. Removal of methylene chloride in vacuo followed by the addition of hot water (10 ml.) gave on cooling white crystals, which were redissolved in hot water and recooled to an oil which rapidly crystallised as the title compound (514 mg.) as off white plates, m.p. 165°–168° dec. > 80% purity. (some contamination with triethylamine hydrochloride).

Preparation 14

1,2,5,6-Tetrahydropyridinyl thioacetic acid

Monochloroacetic acid (8.5 g.) in water (10 ml.) was neutralised with sodium hydroxide (3.6 g.) in water (10 ml.). 1,2,5,6-Tetrahydropyridine (7.57 g.) was added. An exothermic reaction set in and after 30 minutes the pH of he dark red solution had changed from 9 to 8. After 24 hours the reaction mixture was evaporated, the residue was triturated with absolute ethanol (≃ 100 ml.) and filtered. The filtrate was evaporated, barium hydroxide (14 g.) in water (40 ml.) was added to the residue and evaporated repeatedly from water. The residue was redissolved in hot water, treated with $CO_2$ gas, and filtered. The filtrate was evaporated to dryness and the residue, dissolved in hot absolute ethanol, (100 ml.) was acidified to pH 3–4 (2N $H_2SO_4$) and centrifuged to remove inorganic material. The supernatant liquor was evaporated to give 1,2,5,6-tetrahydropyridinyl acetic acid (11.1 g.) as an intractable dark brown gum.

The amino acid (10.7 g.) was stirred in methylene chloride (130 ml.) and triethylamine (10.5 ml.) to give an almost clear solution. The reaction mixture was cooled to 0° and ethyl chloroformate (9.1 ml.) was added dropwise. Triethylamine hydrochloride separated, a further equivalent of triethylamine (10.5 ml.) was added, and the reaction mixture was cooled to −20° during passage of $H_2S$ for 20 minutes. Left to warm to room temperature (1 hour) and excess $H_2S$ was removed in vacuo. Concentrated hydrochloric acid (7.5 ml.) was added and the solvent was removed in vacuo. Water (30 ml.) was added to the brown gelatinous residue which was only partially soluble on warming. The suspension was cooled in ice/water, and the precipitated solid removed by filtration and dried 30°/high vac. to give the title compound (4.0 g.) as a pale brown powder m.p. 165°–170°.

Preparation 15

21-Bromo-2β-ethoxy-3α-hydroxy-5α-pregnane-11,20-dione

2α,3α-Epoxy-5α-pregnane-11,20-dione (500 mg.) was dissolved in dry ethanol (30 ml.), and concentrated sulphuric acid (0.15 ml.) was added. The solution was stirred at 25°–30° for 15 minutes, then water (100 ml.) was added to give a fine crystalline precipitate which was filtered off, washed with water and dried in vacuo over phosphorus pentoxide to give title compound (340 mg.) as white crystals, m.p. 74°–78°, $[\alpha]_D + 100°$.

Bromine (0.53 g.) in methanol (1.45 ml.) was added dropwise to a stirred solution of 3α-hydroxy-2β-ethoxy-5α-pregnane-11,20-dione (2.0 g.) in methanol (15 ml.) containing a trace of acetyl chloride at 0°. The addition took 2 hours and the clear solution was then poured into water and collected by filtration, washed with water and dried in vacuo.

Preparation 16 o-Iodothiobenzoic acid

A solution of sodium hydroxide (10.68 g) in water (14 ml) and alcohol (55 ml) was stirred and treated with hydrogen sulphide at 20° until the mixture did not give an immediate alkaline reaction with phenolphthalein. The solution was cooled to 10°–15° and treated slowly with o-iodobenzoyl chloride (33.66 g). The mixture was stirred for 1¼ hours. The precipitated sodium chloride was filtered off and washed with ethanol (25 ml.) The filtrate was concentrated slightly in vacuo and treated with cold water (80 ml). The solution was covered with ether (100 ml) and stirred while the pH was adjusted to 1.3 with 2N-hydrochloric acid. The ether layer was separated and the aqueous layer was further extracted with ether. The combined ether extracts were washed with water and dried. The ether solution was mixed with water and adjusted to pH 7 with dilute sodium hydroxide solution. The aqueous layer was separated, swirled briefly in vacuo and freeze dried. Trituration of the freeze dried product with ether gave the title compound (28.6 g) as a pale yellow solid. $\nu_{max}$. (Nujol) 15.32 cm$^{-1}$ (COS$^-$).

Preparation 17

21-Bromo-3α-hydroxy-2β-methoxy-5α-pregnan-20-one

A stirred solution of 3α-hydroxy-2β-methoxy-5α-pregnan-20-one (4.0 g.) in dry methanol (300 ml.) was treated at 0° with a solution of bromine (0.65 ml.) in methanol (15 ml.) at such a rate that the yellow colour disappeared before further addition. The mixture was then poured into water and the precipitated solid was collected by filtration, washed with water and dried in vacuo to give title compound (4.0 g) as white crystals.

Preparation 18

21-Bromo-5α-pregnane-3,11,20-trione

21-Bromo-3α-hydroxy-5α-pregnane-11,20-dione (412 mg.) in acetone (20 ml) was stirred during dropwise addition of Jones reagent (0.4 ml) at room temperature. After 10 minutes, the reaction mixture was poured onto water extracted with chloroform and the combined chloroform extract was washed with water, dried (MgSO$_4$) and evaporated. The residue was crystallised from ether/petrol to give title compound (350 mg) as white microcrystals 170°, $[\alpha]_D + 132°$ (c 1.1).

Preparation 19

21-morpholinoacetylthio-5α-pregnane-3,11,20-trione

21-Bromo-5α-pregnane-3,11,20-trione (1.04 g.) was refluxed in dry acetone (100 ml) with morpholino thioacetic acid (600 mg) for 15 minutes. The reaction mixture was concentrated, partitioned between ethyl acetate, water, pH 8, the organic layer was washed, dried (MgSO₄) and evaporated to an off white solid (1.26g.)

A sample was removed and recrystallised from acetone/petrol to give title compound as white prisms m.p. 140°, [α]$_D$ + 113° (c 0.9).

Preparation 20

21-Bromo-3α-hydroxy-2α-methyl-5α-pregnane-11,20-dione

A solution of 3α-hydroxy-2β-methyl-5α-pregnane-11,20-dione (1.04 g.) in dry methanol (150 ml) was stirred at 0°–5° during the dropwise addition of a solution of bromine (0.16 ml) in dry methanol (20 ml) over a period of 2.5 hours. The reaction mixture was partitioned between ethyl acetate and water and the organic layer was separated, washed with water, dried (MgSO₄) and evaporated to a white foam. Purification by preparative t.l.c. (ethyl acetate:benzene 1:2.5) gave the title compound (510 mg.), m.p. 140° dec.; [α]$_D$ + 133° (c 0.95).

We claim:
1. A steroid of formula

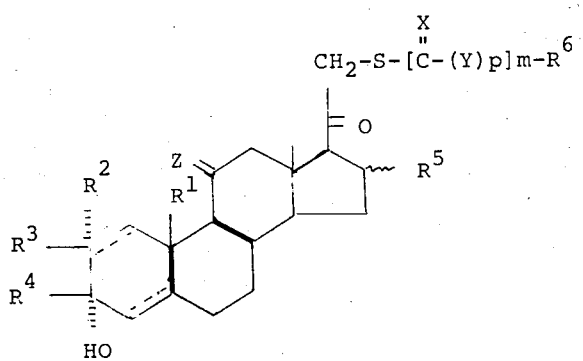

wherein
R¹ is a hydrogen or methyl;
R² is hydrogen or methyl;
R³ is hydrogen or when R² is hydrogen, C₁₋₆ alkoxy, C₁₋₆ alkanoyloxy, C₁₋₅ alkyl, thiocyanato or halo;
R⁴ is hydrogen or methyl;
R⁵ is hydrogen, methyl in either the α or β-configuration
or a gem-dimethyl group;
Z represents two hydrogen atoms or an oxo group;
Each of X and Y is a sulphur or oxygen;
Each of m and p is 0 to 1;
R⁶ is C₁₋₆ alkyl, C₁₋₆ alkyl substituted by halogen or a 5 or 6-membered N-attached, heterocyclic group which may contain a further heteronitrogen, oxygen or sulphur atom, or a C₁₋₆ dialkylamino group; cyclohexyl; phenyl, phenyl substituted by a C₁₋₆ alkyl, C₁₋₆ alkylthio, alkoxycarbonyl the alkyl portion of which contains 1-6 carbon atoms or a nitro group or a halogen atom; benzyl; pyridyl or when m=1 and p=0 an N-attached, 5 or 6 membered, heterocyclic group which may contain a further nitrogen, oxygen or sulphur atom, or when m=0 a cyano group or hydrogen; there being a 5α-hydrogen atom when a 21-acetylthio group is present in a saturated or otherwise unsubstituted 3α-hydroxy-pregnane-11, 20-dione or, where the steriod carries a basic group, a physiologically acceptable acid addition salt thereof; the dotted lines representing a double bond at either one of these positions.

2. A steroid as claimed in claim 1 which possesses 5α-hydrogen atom.

3. A steroid as claimed in claim 1 which possesses an 11-oxo group.

4. A steroid as claimed in claim 1 wherein R¹ is methyl; R² is hydrogen; R³ is hydrogen, C₁ — C₆ alkoxy or C₁ — C₅ alkyl; R⁴ is hydrogen or methyl; R⁵ is hydrogen and wherein the bond at the 1,2-position is a single or double bond.

5. A steroid as claimed in claim 1 wherein X is sulphur when p is 1.

6. A steroid as claimed in claim 1 wherein the 21-substituent is a group of the formula —SCN, —SCO.R¹, —SCS.OR², —SR³ (including SH), —SCS.R², —SCS.SR³, —SO.R³, or —SO₂.R³, where R¹, R² and R³ are substituents R⁶ defined in claim 1.

7. A steroid as claimed in claim 6 wherein the 21-substituent is an acylthio group of the formula —S-CO.R¹ wherein R¹ is an alkyl group of 1–6 C atoms or such a group substituted by an amino group in which the nitrogen atom is a member of a 5 or 6 membered ring which may contain a further heteronitrogen, oxygen or sulfur atom; a phenyl group or such a group substituted by an alkyl, alkylthio, alkoxycarbonyl or nitro group or a halogen atom said alkyl group and the alkyl moiety of said alkylthio and alkoxycarbonyl groups being of 1–6 C atoms; or a pyridyl group.

8. A steroid as claimed in claim 7 wherein the amino group is a morpholino or thiamorpholino group.

9. A steroid as claimed in claim 6 wherein R¹ is a haloalkyl group of 1–6 C atoms.

10. A steroid as claimed in claim 6 wherein the 21-substituent is a group of the formula —SCS.OR² wherein R² is a group —R⁶NR⁷R⁸ in which R⁶ is alkylene of 1–6 C atoms and R⁷ and R⁸ together with the nitrogen atom to which they are attached are a morpholino or thiamorpholino group.

11. A steroid as claimed in claim 6 wherein the 21-substituent is a group of the formula —SCS.R² wherein R² is a group —NR⁷R⁸ in which R⁷ and R⁸ are each an alkyl group of 1–6 C atoms or together with the nitrogen atom to which they are attached are a morpholino or thiamorpholino group.

12. A steroid as claimed in claim 6 wherein R³ is an alkyl group of 1–6 C atoms, an aminoalkyl group in which the alkyl moiety is of 1–6 C atoms and the amino nitrogen atom is a member of a morpholino or thiamorpholino group, a pyridyl or benzyl group.

13. A steroid as claimed in claim 1 which possesses a basic nitrogen atom and is in the form of its hydrochloride, hydrobromide, phosphate, sulphate, p-toluene sulphonate, methane sulphonate, citrate, tartrate, acetate, ascorbate, lactate, maleate or succinate.

14. A steroid as claimed in claim 1 which is 3α-hydroxy-21-thiocyanato-5α-pregnane-11,20-dione; 21-acetylthio-3α-hydroxy-5α-pregnane-11,20-dione; 21-acetylthio-2β-methoxy-3α-hydroxy-5α-pregnane-11,20-dione; 3α-hydroxy-21-pyrid-3′-ylcarbonylthio-5α-pregnane-11,20-dione or a physiologically acceptable acid addition salt thereof;
3α-hydroxy-21-benzoylthio-5α-pregnane-11,20-dione;
3α-hydroxy-21-morpholinoacetylthio-5α-pregnane-11,20-dione or a physiologically acceptable acid addition salt thereof;

3α-hydroxy-21-morpholinoacetylthio-5α-pregn-1-ene-11,20-dione or a physiologically acceptable acid addition salt thereof;

2β-ethoxy-3α-hydroxy-21-morpholinoacetylthio-5α-pregnane-11,20-dione or a physiologically acceptable acid addition salt thereof;

3α-hydroxy-21(2'-morpholino-n-valerylthio)-5α-pregnane-11,20-dione or a physiologically acceptable acid addition salt thereof;

3α-hydroxy-3β-methyl-21-morpholinoacetylthio-5α-pregnane-11,20-dione or a physiologically acceptable acid addition salt thereof;

3α-hydroxy-21-thiamorpholinoacetylthio-5α-pregnane-11,20-dione or a physiologically acceptable acid addition salt thereof; or 3α-hydroxy-21-morpholinoethoxythiocarbonylthio-5α-pregnane-11,20-dione or a physiologically acceptable acid addition salt thereof.

15. A steroid as claimed in claim 1, which is
21-(3'-Chloro-n-propionylthio)-3α-hydroxy-5α-pregnane-11,20-dione; or
21-(N-butyrylthio)-3α-hydroxy-5α-pregnane-11,20-dione.

16. A process for the preparation of a steroid as claimed in claim 1, comprising reacting a corresponding steroid possessing a readily eliminatable substituent at the 21-position, with a compound containing in ionic form the group $$X$$

-continued
$$-S-[C-CY)_p]_mR$$

wherein X, Y, p and m have the meanings given in claim 1 whereby said group is introduced at the 21-position.

17. A process as claimed in claim 16 wherein said compound with which the corresponding steroid is reacted is a salt of an acid of the formula $HSCOR^1$, $HSCS.OR^2$, $HSCSR^2$, $HSCS.SR^3$ or $HSCN R^1$, $R^2$ and $R^3$ being as defined in claim 8.

18. A process as claimed in claim 16 wherein a 21-acylthio is formed and is subsequently hydrolysed to provide a compound having a 21-SH group.

19. A process as claimed in claim 18 wherein the compound having the 21-SH group is subsequently acylated to provide a 21-acylthio compound.

20. A process as claimed in claim 16 wherein the corresponding steroid is reacted with a thiol in the presence of a base whereby a thioether is produced.

21. Steroids as claimed in claim 8 wherein $R^6$ is methyl, phenyl, o-iodophenyl, o-nitrophenyl, o-ethoxycarbonylphenyl, morpholino-methyl, 1'morpholino-n-butyl, thiamorpholinomethyl, 2'-chloroethyl, n-propyl, n-butyl, pyrid-2-yl, pyrid-3-yl, piperidinomethyl, 1,2,5,6-tetrahydropyridinomethyl or 2'morpholinoethyl group.

22. Steroids as claimed in claim 12 wherein $R^3$ is an isopropyl, ethyl, morpholinoethyl, pyrid-2-yl or benzyl group.

* * * * *